United States Patent
Tsutsumi et al.

(10) Patent No.: US 6,506,588 B2
(45) Date of Patent: Jan. 14, 2003

(54) LIPOLYTIC ENZYMES

(75) Inventors: Noriko Tsutsumi, Ichikawa (JP); Yukiko Sasaki, Ichikawa (JP)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/892,188

(22) Filed: Jun. 26, 2001

(65) Prior Publication Data

US 2002/0168746 A1 Nov. 14, 2002

Related U.S. Application Data

(60) Provisional application No. 60/215,462, filed on Jun. 30, 2000.

(30) Foreign Application Priority Data

Jun. 26, 2000 (DK) .......................... 2000 00989

(51) Int. Cl.⁷ ................................. C12N 9/20
(52) U.S. Cl. .................. 435/198; 426/549; 510/108; 510/320; 536/23.2
(58) Field of Search ................. 435/198; 536/23.2; 426/549; 510/108, 320

(56) References Cited

U.S. PATENT DOCUMENTS 5,830,736 A   11/1998   Oxenboll et al. ............ 435/198
5,990,069 A   11/1999   Andre et al. ................. 510/281

FOREIGN PATENT DOCUMENTS

WO   WO 98/26057   6/1998

OTHER PUBLICATIONS

Roberts et al., Mycologia, 79(2), 1987, pp. 265–273.
Shimada et al., Journal or Fermentation and Bioengineering., vol. 78, No. 5, 349–352, 1993.
Nagao et al., J. Biochem., 116, 536–540 (1994).
Satyanarayana et al., Current Science, 1981, vol. 50, No. 15, 680–682.

*Primary Examiner*—Nashaat T. Nashed
(74) *Attorney, Agent, or Firm*—Jason I. Garbell

(57) ABSTRACT

The present invention relates to lipolytic enzymes and DNA sequences encoding same. More specifically, the present invention relates to the lipolytic enzyme and DNA sequences encoding same isolated from *Fusarium sulphureum* and analogues thereof.

6 Claims, No Drawings

SEQUENCE LISTING

<160> NUMBER OF SEQ ID NOS: 12

<210> SEQ ID NO 1
<211> LENGTH: 1161
<212> TYPE: DNA
<213> ORGANISM: Fusarium sulphureum
<220> FEATURE:
<221> NAME/KEY: CDS
<222> LOCATION: (1)..(94)
<223> OTHER INFORMATION:

```
<220> FEATURE:
<221> NAME/KEY: CDS
<222> LOCATION: (147)..(312)
<223> OTHER INFORMATION:
<220> FEATURE:
<221> NAME/KEY: CDS
<222> LOCATION: (369)..(1158)
<223> OTHER INFORMATION:
<220> FEATURE:
<221> NAME/KEY: mat_peptide
<222> LOCATION: (94)..()
<223> OTHER INFORMATION:

<400> SEQUENCE: 1 atg ctc ctc cta cca ctc ctc tca gcc gtc act ctc gcg gta gca agt        48
Met Leu Leu Leu Pro Leu Leu Ser Ala Val Thr Leu Ala Val Ala Ser
    -30              -25                 -20 cca cta gct tcc gtc gaa gag tac gcc aag tct ctc gaa gac aga g          94
Pro Leu Ala Ser Val Glu Glu Tyr Ala Lys Ser Leu Glu Asp Arg
-15              -10                  -5                  -1 gtaagcacca aactctcctc catatcatgc tatatactca tcacactccc ag ct gtg       151
                                                         Ala Val act gtg tct tcg tca gac tac aac aac ttc aag ttc tac atc caa cat       199
Thr Val Ser Ser Ser Asp Tyr Asn Asn Phe Lys Phe Tyr Ile Gln His
        5                  10                  15 ggc gcc gca gca tac tgt aac tcc gaa gcc tca gct ggc gca aag atc       247
Gly Ala Ala Ala Tyr Cys Asn Ser Glu Ala Ser Ala Gly Ala Lys Ile
 20                  25                  30 acc tgc gca agc aac ggt tgt cca acc gtc cag tcc aac ggc gca acc       295
Thr Cys Ala Ser Asn Gly Cys Pro Thr Val Gln Ser Asn Gly Ala Thr
35                  40                  45                  50 atc gtg gca tcc ttc ct gtaagtcacg cccagtcaca aacatctcat               342
Ile Val Ala Ser Phe Leu
                    55 acctcatact tatatgactt cttcag t ggt tcc aag act ggc atc ggc ggt        393
                              Gly Ser Lys Thr Gly Ile Gly Gly
                                                          60 tat gtc gca aca gat tca tcc cgc aag gaa atc gtc gtc tcg atc cgt       441
Tyr Val Ala Thr Asp Ser Ser Arg Lys Glu Ile Val Val Ser Ile Arg
65                  70                  75                  80 gga agc agc aac atc cgc aac tgg ctt aca aac ctc gac ttt gac cag       489
Gly Ser Ser Asn Ile Arg Asn Trp Leu Thr Asn Leu Asp Phe Asp Gln
                 85                  90                  95 tcc gac tgc agc ttg acc tcc ggc tgc ggc gta cac tcg ggc ttc cag       537
Ser Asp Cys Ser Leu Thr Ser Gly Cys Gly Val His Ser Gly Phe Gln
             100                 105                 110 aac gcc tgg gac gag atc tcg gag aga gcc act gct gct gtg gcc aag       585
Asn Ala Trp Asp Glu Ile Ser Glu Arg Ala Thr Ala Ala Val Ala Lys
         115                 120                 125 gca cgc aag gca aac tct ggt ttc aag gtc att gct aca ggc cac tcc       633
Ala Arg Lys Ala Asn Ser Gly Phe Lys Val Ile Ala Thr Gly His Ser
     130                 135                 140 ctc ggt ggt gcg gtc gct aca ttg gct gct gcg aat ctg agg gtt ggt       681
Leu Gly Gly Ala Val Ala Thr Leu Ala Ala Ala Asn Leu Arg Val Gly
145                 150                 155                 160 ggc aca ccc gtg gac atc tac acg tac ggt gct cct cga gtg ggc aac       729
Gly Thr Pro Val Asp Ile Tyr Thr Tyr Gly Ala Pro Arg Val Gly Asn
                165                 170                 175 gcc cag ctt tca gcg ttc atc tcg aac caa gct ggc ggg gaa tat cgc       777
Ala Gln Leu Ser Ala Phe Ile Ser Asn Gln Ala Gly Gly Glu Tyr Arg
            180                 185                 190 gtt act cac gcc aga gac ccc gtg cct cgt ctg ccc cct ctg gtg ttt       825
```

-continued

```
Val Thr His Ala Arg Asp Pro Val Pro Arg Leu Pro Pro Leu Val Phe
        195                 200                 205 gga tac agg cac act tcg ccc gag tac tgg cta tct ggc ggc ggt ggc       873
Gly Tyr Arg His Thr Ser Pro Glu Tyr Trp Leu Ser Gly Gly Gly Gly
        210                 215                 220 gac aag att gat tat acc atc agc gat atc aag gtc tgt gag ggc gcc       921
Asp Lys Ile Asp Tyr Thr Ile Ser Asp Ile Lys Val Cys Glu Gly Ala
225                 230                 235                 240 gct aat ctc cag tgt aac ggt ggc acg ctg ggt ttg gac att gcg gct       969
Ala Asn Leu Gln Cys Asn Gly Gly Thr Leu Gly Leu Asp Ile Ala Ala
                245                 250                 255 cat ctg cat tac ttc cag cac act gat gct tgc tcg gcg gga ggc att      1017
His Leu His Tyr Phe Gln His Thr Asp Ala Cys Ser Ala Gly Gly Ile
        260                 265                 270 tct ttt aga cga tac agg agt gct aag cgt gaa ggt atc gcc aag agg      1065
Ser Phe Arg Arg Tyr Arg Ser Ala Lys Arg Glu Gly Ile Ala Lys Arg
        275                 280                 285 gct gat atg tcg gat gct gag ctg gag aag aag ctc aac tct tat gtt      1113
Ala Asp Met Ser Asp Ala Glu Leu Glu Lys Lys Leu Asn Ser Tyr Val
290                 295                 300 gag atg gat aag gag tat gtg gat agc cat aag aat cgt tca tca taa      1161
Glu Met Asp Lys Glu Tyr Val Asp Ser His Lys Asn Arg Ser Ser
305                 310                 315
```

<210> SEQ ID NO 2
<211> LENGTH: 350
<212> TYPE: PRT
<213> ORGANISM: Fusarium sulphureum

<400> SEQUENCE: 2

```
Met Leu Leu Pro Leu Leu Ser Ala Val Thr Leu Ala Val Ala Ser
        -30                 -25                 -20

Pro Leu Ala Ser Val Glu Glu Tyr Ala Lys Ser Leu Glu Asp Arg Ala
-15                 -10                  -5                 -1   1

Val Thr Val Ser Ser Ser Asp Tyr Asn Asn Phe Lys Phe Tyr Ile Gln
                 5                  10                  15

His Gly Ala Ala Ala Tyr Cys Asn Ser Glu Ala Ser Ala Gly Ala Lys
        20                  25                  30

Ile Thr Cys Ala Ser Asn Gly Cys Pro Thr Val Gln Ser Asn Gly Ala
        35                  40                  45

Thr Ile Val Ala Ser Phe Leu Gly Ser Lys Thr Gly Ile Gly Gly Tyr
50                  55                  60                  65

Val Ala Thr Asp Ser Ser Arg Lys Glu Ile Val Ser Ile Arg Gly
                70                  75                  80

Ser Ser Asn Ile Arg Asn Trp Leu Thr Asn Leu Asp Phe Asp Gln Ser
                85                  90                  95

Asp Cys Ser Leu Thr Ser Gly Cys Gly Val His Ser Gly Phe Gln Asn
                100                 105                 110

Ala Trp Asp Glu Ile Ser Glu Arg Ala Thr Ala Val Ala Lys Ala
        115                 120                 125

Arg Lys Ala Asn Ser Gly Phe Lys Val Ile Ala Thr Gly His Ser Leu
130                 135                 140                 145

Gly Gly Ala Val Ala Thr Leu Ala Ala Asn Leu Arg Val Gly Gly
                150                 155                 160

Thr Pro Val Asp Ile Tyr Thr Tyr Gly Ala Pro Arg Val Gly Asn Ala
                165                 170                 175

Gln Leu Ser Ala Phe Ile Ser Asn Gln Ala Gly Gly Glu Tyr Arg Val
```

```
              180                 185                 190
Thr His Ala Arg Asp Pro Val Pro Arg Leu Pro Pro Leu Val Phe Gly
            195                 200                 205

Tyr Arg His Thr Ser Pro Glu Tyr Trp Leu Ser Gly Gly Gly Gly Asp
210                 215                 220                 225

Lys Ile Asp Tyr Thr Ile Ser Asp Ile Lys Val Cys Glu Gly Ala Ala
                230                 235                 240

Asn Leu Gln Cys Asn Gly Gly Thr Leu Gly Leu Asp Ile Ala Ala His
            245                 250                 255

Leu His Tyr Phe Gln His Thr Asp Ala Cys Ser Ala Gly Gly Ile Ser
            260                 265                 270

Phe Arg Arg Tyr Arg Ser Ala Lys Arg Glu Gly Ile Ala Lys Arg Ala
        275                 280                 285

Asp Met Ser Asp Ala Glu Leu Glu Lys Lys Leu Asn Ser Tyr Val Glu
290                 295                 300                 305

Met Asp Lys Glu Tyr Val Asp Ser His Lys Asn Arg Ser Ser
                310                 315
```

<210> SEQ ID NO 3
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n = Inosine
<220> FEATURE:
<221> NAME/KEY: misc_feature
<222> LOCATION: (6)..(6)
<223> OTHER INFORMATION: n = Inosine
<220> FEATURE:
<221> NAME/KEY: misc_feature
<222> LOCATION: (9)..(9)
<223> OTHER INFORMATION: n = Inosine
<220> FEATURE:
<221> NAME/KEY: misc_feature
<222> LOCATION: (15)..(15)
<223> OTHER INFORMATION: n = Inosine
<220> FEATURE:
<221> NAME/KEY: misc_feature
<222> LOCATION: (18)..(18)
<223> OTHER INFORMATION: n = Inosine

<400> SEQUENCE: 3
ccnccnarns wrtgnccngt                                              20

<210> SEQ ID NO 4
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n = Inosine
<220> FEATURE:
<221> NAME/KEY: misc_feature
<222> LOCATION: (9)..(9)
<223> OTHER INFORMATION: n = Inosine
<220> FEATURE:
<221> NAME/KEY: misc_feature
<222> LOCATION: (12)..(12)
<223> OTHER INFORMATION: n = Inosine
<220> FEATURE:
<221> NAME/KEY: misc_feature

```
<222> LOCATION: (16)..(16)
<223> OTHER INFORMATION: n = Inosine
<220> FEATURE:
<221> NAME/KEY: misc_feature
<222> LOCATION: (17)..(17)
<223> OTHER INFORMATION: n = Inosine
<220> FEATURE:
<221> NAME/KEY: misc_feature
<222> LOCATION: (18)..(18)
<223> OTHER INFORMATION: n = Inosine
<220> FEATURE:
<221> NAME/KEY: misc_feature
<222> LOCATION: (21)..(21)
<223> OTHER INFORMATION: n = Inosine

<400> SEQUENCE: 4
ggntgyggng tncaynnngg ntt                                         23

<210> SEQ ID NO 5
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n = Inosine
<220> FEATURE:
<221> NAME/KEY: misc_feature
<222> LOCATION: (9)..(9)
<223> OTHER INFORMATION: n = Inosine
<220> FEATURE:
<221> NAME/KEY: misc_feature
<222> LOCATION: (15)..(15)
<223> OTHER INFORMATION: n = Inosine
<220> FEATURE:
<221> NAME/KEY: misc_feature
<222> LOCATION: (18)..(18)
<223> OTHER INFORMATION: n = Inosine

<400> SEQUENCE: 5
ggrtcntyns crtkngtnac                                             20

<210> SEQ ID NO 6
<211> LENGTH: 44
<212> TYPE: DNA
<213> ORGANISM: Artificial Sequence
<220> FEATURE:
<223> OTHER INFORMATION: Primer

<400> SEQUENCE: 6
ctaatacgac tcactatagg gctcgagcgg ccgcccgggc aggt                  44

<210> SEQ ID NO 7
<211> LENGTH: 8
<212> TYPE: DNA
<213> ORGANISM: seq 8

<400> SEQUENCE: 7 acctgccc                                                          8

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
```

-continued

```
tggacaaccg ttccttgcgc a                                              21

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
tacacgtacg gtgctcctcg agtgg                                          25

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
tatctggcgg cggtggcgac                                                20

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
cgcggatcca tgctcctcct accactcctc tcagcc                              36

<210> SEQ ID NO 12
<211> LENGTH: 48
<212> TYPE: DNA
<213> ORGANISM: Artificial Sequence
<220> FEATURE:
<223> OTHER INFORMATION: Primer

<400> SEQUENCE: 12
acgcgtcgac ttatgatgaa cgattcttat ggctatccac atactcct                 48
```

LIPOLYTIC ENZYMES

CROSS-REFERENCE TO RELATED APPLICATIONS

This application claims under 35 U.S.C. 119 priority from Danish application no. PA 2000 00989, filed on Jun. 26, 2000, and the benefit of U.S. provisional application No. 60/215,462, filed Jun. 30, 2000, the contents of which are fully incorporated herein by reference.

FIELD OF THE INVENTION

The present invention relates to lipolytic enzymes, methods of using and producing lipolytic enzymes, as well as a nucleic acid sequence encoding lipolytic enzymes.

BACKGROUND OF THE INVENTION

Lipolytic enzymes (such as lipases and phospholipases) are capable of hydrolyzing carboxylic ester bonds in a substrate to release carboxylic acids. They are known to be useful, e.g., in baking and detergents.

A lipase/phospholipase from *Fusarium oxysporum* and its sequence are known. WO 98/26057.

SUMMARY OF THE INVENTION

The inventors have isolated a lipolytic enzyme from *Fusarium sulphureum*. The inventors also isolated the gene encoding the novel lipolytic enzyme and cloned it into an *E. coli* strain.

Accordingly, the invention provides a lipolytic enzyme which may be a polypeptide having an amino acid sequence as the mature peptide shown in SEQ ID NO: 1.

Further, the lipolytic enzyme of the invention may be a polypeptide encoded by the lipolytic enzyme encoding part of the DNA sequence cloned into a plasmid present in *Escherichia coli* deposit number DSM 13539.

The lipolytic enzyme may also be an analogue of the polypeptide defined above which:

i) has at least 85% homology with said polypeptide, ii) is immunologically reactive with an antibody raised against said polypeptide in purified form, iii) is an allelic variant of said polypeptide, Finally, the lipolytic enzyme of the invention may be a polypeptide which is encoded by a nucleic acid sequence which hybridizes under high stringency conditions with a complementary strand of the nucleic acid sequence of SEQ ID NO: 1 encoding the mature polypeptide or a subsequence thereof having at least 100 nucleotides.

The nucleic acid sequence of the invention may comprise a nucleic acid sequence which encodes the lipolytic enzyme described above, or it may encode a lipolytic enzyme and comprise:

a) the DNA sequence encoding a mature lipolytic enzyme cloned into a plasmid present in *Escherichia coli* DSM 13539, b) the DNA sequence encoding a mature lipolytic enzyme shown in SEQ ID NO: 1, or c) an analogue of the DNA sequence defined in a) or b) which
   i) has at least 80% homology with said DNA sequence, or
   ii) hybridizes at high stringency with said DNA sequence, its complementary strand or a subsequence thereof.

Other aspects of the invention provide a recombinant expression vector comprising the DNA sequence, and a cell transformed with the DNA sequence or the recombinant expression vector.

A comparison with full-length prior-art sequences shows that the mature amino acid sequence of the invention has 82% homology with the lipase/phospholipase from *Fusarium oxysporum* described above, and the corresponding DNA sequence of the invention shows 77% homology with that of the *F. oxysporum* enzyme.

DETAILED DESCRIPTION OF THE INVENTION

Genomic DNA Source

A lipolytic enzyme of the invention may be derived from a strain of Fusarium, particularly *F. sulphureum*, using probes designed on the basis of the DNA sequences in this specification.

A strain of *Escherichia coli* containing a gene encoding lipolytic enzyme was deposited by the inventors under the terms of the Budapest Treaty with the DSMZ—Deutshe Sammmlung von Microorganismen und Zellkulturen GmbH, Mascheroder Weg 1b, D-38124 Braunschweig DE, Germany. The deposit date was Jun. 15, 2000, and the accession number was DSM 13539.

Properties of Lipolytic Enzyme

The lipolytic enzyme is able to hydrolyze carboxylic ester bonds and is classified as EC 3.1.1 according to Enzyme Nomenclature 1992, Academic Press, Inc. The enzyme has lipase (triacylglycerol lipase) activity (EC 3.1.1.3) and may also have phospholipase activity.

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The lipolytic enzyme of the invention may be produced by transforming a suitable host cell with a DNA sequence encoding the lipolytic enzyme, cultivating the transformed organism under conditions permitting the production of the enzyme, and recovering the enzyme from the culture.

The host organism is preferably a eukaryotic cell, in particular a fungal cell, such as a yeast cell or a filamentous fungal cell, e.g. a strain of Aspergillus, Fusarium, Trichoderma or Saccharomyces, particularly *A. niger, A. oryzae, F. graminearum, F. sambucinum, F. cerealis* or *S. cerevisiae*. The production of the lipolytic enzyme in such host organisms may be done by the general methods described in EP 238,023 (Novo Nordisk), WO 96/00787 (Novo Nordisk) or EP 244,234 (Alko).

Hybridization

The hybridization is used to indicate that a given DNA sequence is analogous to a nucleotide probe corresponding to a DNA sequence of the invention. The hybridization conditions are described in detail below.

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a random-primed (Feinberg, A. P. and Vogelstein, B. (1983) *Anal. Biochem.* 132:6–13), $^{32}$P-dCTP-labeled (specific activity >1×10$^9$ cpm/µg) probe for 12 hours at approx. 45° C. The filter is then washed two times for 30 minutes in 2×SSC, 0.5% SDS at a temperature of at least 55° C., more preferably at least 60° C., more preferably at least 65° C., even more preferably at least 70° C., especially at least 75° C.

Molecules to which the oligonucleotide probe hybridizes under these conditions are detected using a x-ray film.

Alignment and Homology

The present invention also includes lipolytic enzymes and nucleotide sequences encoding same that have homology to the disclosed sequences. More preferably, the lipolytic enzymes and the nucleotide sequences of the invention may have homologies to the disclosed sequences of at least 85%, at least 90% or at least 95%, e.g. at least 96%, at least 97%, at least 98%.

For purposes of the present invention, alignments of sequences and calculation of homology scores were done using a Needleman-Wunsch alignment (i.e. global alignment), useful for both protein and DNA alignments. The default scoring matrices BLOSUM50 and the identity matrix are used for protein and DNA alignments respectively. The penalty for the first residue in a gap is –12 for proteins and –16 for DNA, while the penalty for additional residues in a gap is –2 for proteins and –4 for DNA. Alignment is from the FASTA package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA", Methods in Enzymology, 183:63–98).

Lipase Activity (LU)

A substrate for lipase is prepared an emulsion of 5% by volume of tributyrin (glycerin tributyrate) using 0.1% gum Arabic as emulsifier. The hydrolysis of tributyrin at 30° C. at pH 7 is followed in a pH-stat titration experiment. One unit of lipase activity (1 LU) equals the amount of enzyme capable of releasing 1 µmol butyric acid/min at the standard conditions. 1 KLU=1000 LU.

Use of Lipolytic Enzyme

The lipolytic enzyme of the invention can be used in various industrial application of lipolytic enzymes, e.g. in baking, detergents, diglyceride synthesis (EP 307154), acidolysis, interesterification (WO 8802775), ester hydrolysis, oil degumming (JP-A 2-153997, U.S. Pat. No. 5,264,367), production of lysolecithin (JP patent 2794574, JP-B 6-087751) and in the process described in PCT/DK 00/00109.

Use in Baking

The lipolytic enzyme of the invention can be used in the preparation of dough, bread and cakes, e.g. to improve the elasticity of the bread or cake. Thus, the lipolytic enzyme can be used in a process for making bread, comprising adding the lipolytic enzyme to the ingredients of a dough, kneading the dough and baking the dough to make the bread. This can be done in analogy with WO 9404035 and EP 585988.

Use in Detergent

The variant may be used as a detergent additive, e.g. at a concentration (expressed as pure enzyme protein) of 0.001–10 (e.g. 0.01–1) mg per gram of detergent or 0.001–100 (e.g. 0.01–10) mg per liter of wash liquor.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in WO 97/04079, WO 97/07202, WO 97/41212, PCT/DK WO 98/08939 and WO 97/43375.

The detergent composition of the invention may particularly be formulated for hand or machine dishwashing operations. e.g. as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

MATERIALS AND METHODS

Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for Bacillus". John Wiley and Sons, 1990.

Enzymes

Enzymes for DNA manipulations (e.g. restriction endonucleases, ligases etc.) are obtainable from New England Biolabs, Inc. and were used according to the manufacturer's instructions.

Plasmids/vectors pT7Blue (Invitrogen, Netherlands)
pCaHj483 is described in WO 9704079 and WO 9942566.

Cloning

LA PCR™ in vitro Cloning Kit (TaKaRa) was used for cloning and was used according to the manufacturer's instructions.

Microbial Strains

*E. coli* JM109 (TOYOBO, Japan)
*A. oryzae* BECh-2 is described in Danish patent application PA 1999 01726. It is a mutant of JaL 228 (described in WO 98/12300) which is a mutant of IFO 4177.

Media and Reagents

Cove: 342.3 g/L Sucrose, 20 ml/L COVE salt solution, 10 mM Acetamide, 30 g/L noble agar.
Cove-2: 30 g/L Sucrose, 20 ml/L COVE salt solution, 10 mM, Acetamide, 30 g/L noble agar.
Cove salt solution: per liter 26 g KCl, 26 g MgSO4-7aq, 76 g KH2PO4, 50 ml Cove trace metals.
Cove trace metals: per liter 0.04 g NaB407-10aq, 0.4 g CuSO4-5aq, 1.2 g FeSO4-7aq, 0.7 g MnSO4-aq, 0.7 g Na2MoO2-2aq, 0.7 g ZnSO4-7aq.
AMG trace metals: per liter 14.3 g ZnSO4-7aq, 2.5 g CuSO4-5aq, 0.5 g NiCl2, 13.8 g FeSO4, 8.5 g MnSO4, 3.0 g citric acid.
YPG: 4 g/L Yeast extract, 1 g/L KH2PO4, 0.5 g/L MgSO4-7aq, 5 g/L Glucose, pH 6.0.
STC: 0.8 M Sorbitol, 25 mM Tris pH 8, 25 mM CaCl2.
STPC: 40% PEG4000 in STC buffer.
Cove top agarose: 342.3 g/L Sucrose, 20 ml/L COVE salt solution, 10 mM Acetamide, 10 g/L low melt agarose.
MS-9: per liter 30 g soybean powder, 20 g glycerol, pH 6.0.
MDU-pH5: per liter 45 g maltose-1aq, 7 g yeast extract, 12 g KH2PO4, 1 g MgSO4-7aq, 2 g K2SO4, 0.5 ml AMG trace metal solution and 25 g 2-morpholinoethanesulfonic acid, pH 5.0.

EXAMPLES

Example 1

Cloning and Expression of Lipase Gene from *Fusarium sulphureum*

Transformation in Aspergillus Strain

*Aspergillus oryzae* strain BECh-2 was inoculated to 100 ml of YPG medium and incubated for 16 hrs at 32° C. at 120 rpm. Pellets were collected and washed with 0.6 M KCl, and resuspended 20 ml 0.6 M KCl containing a commercial β-glucanase product (Glucanex, product of Novo Nordisk A/S) at the concentration of 30 μl/ml. Cultures were incubated at 32° C. at 60 rpm until protoplasts formed, then washed with STC buffer twice. The protoplasts were counted with a hematometer and resuspended in an 8:2:0.1 solution of STC:STPC:DMSO to a final concentration of 2.5×10e7 protoplasts/ml. About 3 μg of DNA was added to 100 μl of protoplasts solution, mixed gently and incubated on ice for 30 min. One ml of SPTC was added and incubated 30 min at 37° C. After the addition of 10 ml of 50° C. Cove top agarose, the reaction was poured onto Cove agar plate. Transformation plates were incubated at 32° C. for 5 days.

PCR Screening of Lipase

PCR reactions on *Fusarium sulphureum* genomic DNA was done with two following primer sets: lip3/lip15 and lip10/lip17 designed based upon the alignment of 3 lipases from Fusarium.

| lip3: 5'-carcayggicgcigcigcitaytg-3' | (SEQ ID NO: 3) |
| lip15: 5'-ccicciariswrtgiccigt-3' | (SEQ ID NO: 4) |
| lip10: 5'-ggitgyggigticayiiiggitt-3' | (SEQ ID NO: 5) |
| lip17: 5'-ggrtcityiscrtkigtiac-3' | (SEQ ID NO: 6) |

Reaction components (2.6 ng/μl of genomic DNA, 250 mM dNTP each, primer 250 nM each, 0.1 U/μl of Taq polymerase in 1×buffer (Roche Diagnostics, Japan)) were mixed and submitted for PCR under the following conditions.

| Step | Temperature | Time |
|---|---|---|
| 1 | 94° C. | 1 min |
| 2 | 50° C. | 1 min |
| 3 | 72° C. | 2 min |
| 4 | 72° C. | 10 min |
| 5 | 4° C. | forever |

Steps 1 to 3 were repeated 30 times.

450 bp of fragment and 280 bp of fragment were amplified from primer sets of lip3/lip15 and lip10/lip17, respectively. They were gel-purified with GFX™ PCR DNA and Gel Band Purification kit (amersham pharmacia biotech) and ligated into a pT7Blue vector with ligation high (TOYOBO, Japan). The ligation mixtures were transformed into *E. coli* JM109. The resultant plasmids, pT27-0315 and pT27-1017, were sequenced and compared to the *Fusarium oxysporum* lipase, showing that a clone encodes the internal part of the lipase.

Cloning of Lipase Gene

In order to clone the missing part of the lipase gene, adaptor PCR was done. A cassette was made by mixing of adaptor L and adaptor S.

| adaptor L: 5'-ctaatacgactcactatagggctcgagcggccg cccgggcaggt=3' | (SEQ ID NO: 7) |
| adaptor S: 5'-acctgccc-3' | (SEQ ID NO: 8) |

3' and 5' of adaptor S are dephosphorylated and amidation, respectively.

1.3 μg of Eco RV digested genome was ligated to the cassette and it was used as a PCR template. Reaction components (7 ng/μl of genomic DNA ligated to cassette, 250 mM dNTP each, primer 250 nM each, 0.05 U/μl of Expand high fidelity polymerase in 1×buffer (Roche Diagnostics, Japan)) were mixed and submitted for PCR under the following conditions.

| Step | Temperature | Time |
|---|---|---|
| 1 | 94° C. | 2 min |
| 2 | 94° C. | 10 sec |
| 3 | 55° C. | 30 sec |
| 4 | 68° C. | 45 sec |
| step 2–4 repeat 10 times | | |
| 5 | 94° C. | 10 sec |
| 6 | 55° C. | 30 sec |
| 7 | 68° C. | 45 sec + 20 sec/cycle |
| step 5–7, repeat 20 times | | |
| 8 | 68° C. | 7 min |
| 7 | 4° C. | forever |

500 bp of DNA fragment corresponding to N-terimal region was obtained with 27N1long primer and 200 bp of DNA fragment corresponding to C-terminal region was obtained with 27C1long primer,

| 27N1long: 5'-tggacaaccgttccttgcgca-3' | (SEQ ID NO: 9) |
| 27C1long: 5'-tacacgtacggtgctcctcgagtgg-3' | (SEQ ID NO: 10) |

Obtained fragments were purified by GFX™ PCR DNA and Gel Band Purification kit (amersham pharmacia biotech) and sequenced with each primers which amplified the fragment.

The missing C-terminal part was cloned with LA PCR™ in vitro Cloning Kit (TaKaRa) following to the manufacturer's instructions. 350 bp of DNA fragment corresponding to C-terminal region was obtained from Xho I digested genome ligated to Sal I cassette of the kit with 27C2 primer.

27C2: 5'-tatctggcggcggtggcgac-3' (SEQ ID NO: 11)

Obtained fragments were purified by GFX™ PCR DNA and Gel Band Purification kit (amersham pharmacia biotech) and sequenced with 27C2 primer.

The fidelity of taq polymerase is not good so in order to get the right sequence whole gene was amplified the following primers.

27N(Bam): 5'-cgcggatccatgctcctcctaccactcct
ctcagcc-3' (SEQ ID NO: 12)

27C(Sal): 5'-acgcgtcgacttatgatgaacgattcttatgg
ctatccacatactcct-3' (SEQ ID NO 13)

Reaction components (6 ng/µl of genomic DNA, 250 mM dNTP each, primer 250 nM each, 0.05 U/µl of Expand high fidelity polymerase in 1×buffer (Roche Diagnostics, Japan)) were mixed and submitted for PCR under the following conditions.

| Step | Temperature | Time |
|---|---|---|
| 1 | 94° C. | 2 min |
| 2 | 94° C. | 10 sec |
| 3 | 55° C. | 30 sec |
| 4 | 68° C. | 45 sec |
| step 2–4 repeat 10 times | | |
| 5 | 94° C. | 10 sec |
| 6 | 55° C. | 30 sec |
| 7 | 68° C. | 45 sec + 20 sec/cycle |
| step 5–7, repeat 20 times | | |
| 8 | 68° C. | 7 min |
| 7 | 4° C. | forever |

Amplified DNA fragment was gel-purified with GFX™ PCR DNA and Gel Band Purification kit (amersham pharmacia biotech) and ligated into a pT7Blue vector with ligation high (TOYOBO, Japan). The ligation mixtures were transformed into *E. coli* JM109. Four plasmids, pT27w-1, pT27w-2, pT27w-3, and pT27w-4, were sequence and their sequence were compared. pT27w-3 has no PCR error and it is defined as *Fusarium sulphureum* lipase nucleotide sequence.

Expression of Lipase Gene in *Aspergillus oryzae*

The lipase gene was digested from pT27w-3 with BamH I and Sal I and ligated into the BamH I and XhoI sites in the Aspergillus expression cassette pCaHj483 which has *Aspergillus niger* neutral amylase promoter, *Aspergillus nidulans* TPI leader sequences, *Aspergillus niger* glucoamylase terminator and *Aspergillus nidulans* amdS gene as a marker. The resultant plasmid was pNL27w-8.

pNL27w-8 was transformed into *Aspergillus oryzae* BECh-2. The selected transformants were inoculated in 100 ml of MS-9 media and cultivated at 30° C. for 1 day. 3 ml of grown cell in MS-9 medium was inoculated to 100 ml of MDU-2BP medium and cultivated at 32° C. for 3 days. The supernatant was obtained by centrifugation.

The lipase productivity of selected transformants was determined as LU activity. The productivity of the best transformant TNL27-75 was 130 LU/ml and BECh2 has no lipase activity.

Example 2

Immunological Characterization of Lipolytic Enzyme

A purified lipolytic enzyme sample having the amino acid sequence shown as amino acids 1–319 of SEQ ID NO: 1 was tested by immunodiffusion against a polyclonal antibody raised against the *Fusarium oxysporum* lipase. No immunological cross-reaction was found.

SEQUENCE LISTING

| | |
|---|---|
| lip3: 5'-carcayggigcigcigcitaytg-3' | (SEQ ID NO: 3) |
| lip15: 5'-ccicciariswrtgiccigt-3' | (SEQ ID NO: 4) |
| lip10: 5'-ggitgyggigticayiiiggitt-3' | (SEQ ID NO: 5) |
| lip17: 5'-ggrtcityiscrtkigtiac-3' | (SEQ ID NO: 6) |
| adaptor L: 5'-ctaatacgactcactatagggctcgagcggc cgcccgggcaggt=3' | (SEQ ID NO: 7) |
| adaptor S: 5'-acctgccc-3' | SEQ ID NO: |
| 27N1long: 5'-tggacaaccgttccttgcgca-3' | (SEQ ID NO: 8) |
| 27C1long: 5'-tacacgtacggtgctcctcgagtgg-3' | (SEQ ID NO: 9) |
| 27C2: 5'-tatctggcggcggtggcgac-3' | (SEQ ID NO:10) |
| 27N(Bam): 5'-cgcggatccatgctcctcctaccactcc tctcagcc-3' | (SEQ ID NO: 11) |
| 27C(Sal): 5'-acgcgtcgacttatgatgaacgattcttatgg ctatccacatactcct-3' | (SEQ ID NO:12) |

What is claimed is:

1. An isolated lipolytic enzyme which is:
   a) a polypeptide encoded by the lipolytic enzyme encoding part of the DNA sequence cloned into a plasmid present in *Escherichia coli* deposit number DSM 13539, or
   b) a polypeptide having an amino acid sequence of the mature peptide shown in SEQ ID NO: 2; or
   c) an analogue of the polypeptide defined in (a) or (b) which has at least 95% homology with said polypeptide, or
   d) a polypeptide which is encoded by a nucleic acid sequence which hybridizes with a complementary strand of the nucleic acid sequence of SEQ ID NO: 1 encoding the mature polypeptide under hybridization conditions comprising prehybridizing in a solution of 5×SSC, 5×Denhardt's solution, 0.5% SDS and 100 µg/ml of denatured sonicated salmon sperm DNA, followed by hybridization in the same solution for 12 hours at approx. 45° C., followed by washing in 2×SSC, 0.5% SDS for 30 minutes at a temperature of at least 70° C.

2. The lipolytic enzyme of claim 1 which is native to a strain of Fusarium.

3. The lipolytic enzyme of claim 1 which is native to a strain of *F. sulphureum*.

4. A method for preparing a dough or a baked product made from the dough, comprising adding the lipolytic enzyme of claim 1 to the dough.

5. A dough composition comprising the lipolytic enzyme of claim 1.

6. A detergent composition comprising a surfactant and the lipolytic enzyme of claim 1.

* * * * *